United States Patent [19]

Kiehs et al.

[11] 4,203,977
[45] May 20, 1980

[54] PHOSPHORIC ACID ESTERS, COMPOSITION AND USE

[75] Inventors: Karl Kiehs, Lampertheim; Heinrich Adolphi, Limburgerhof, both of Fed. Rep. of Germany

[73] Assignee: BASF Aktiengesellschaft, Fed. Rep. of Germany

[21] Appl. No.: 948,152

[22] Filed: Oct. 3, 1978

[30] Foreign Application Priority Data

Oct. 13, 1977 [DE] Fed. Rep. of Germany ....... 2746057

[51] Int. Cl.$^2$ .................. C07F 9/165; A01N 9/36
[52] U.S. Cl. .......................... 424/211; 424/200; 424/210; 260/455 P; 260/938; 260/940; 260/944; 260/945; 544/157
[58] Field of Search .............. 260/944, 945; 424/211

[56] References Cited

U.S. PATENT DOCUMENTS

| 2,578,652 | 12/1951 | Cassaday | 260/461 |
| 3,053,876 | 9/1962 | Malz et al. | 240/944 |
| 3,896,190 | 7/1975 | Beutel et al. | 260/945 |

*Primary Examiner*—Henry R. Jiles
*Assistant Examiner*—R. W. Ramsuer

[57] ABSTRACT

Phosphoric (phosphonic) acid esters of the formula

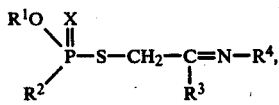

where $R^1$ denotes linear or branched alkyl of up to 4 carbon atoms, $R^2$ denotes linear or branched alkyl, alkoxy or alkylthio, each of up to 4 carbon atoms, mono- or dialkylamino of up to 4 carbon atoms in each alkyl, or phenyl, $R^3$ denotes linear or branched alkoxy or alkylthio of up to 4 carbon atoms, amino, mono- or dialkylamino of up to 4 carbon atoms in each alkyl, alkylalkoxyalkylamino of up to 4 carbon atoms in each alkyl or alkoxyalkyl, dialkoxyalkylamino of up to 4 carbon atoms in each alkoxyalkyl, alkylalkenylamino of up to 4 carbon atoms in each alkyl or alkenyl, alkylalkynylamino of up to 4 carbon atoms in each alkyl or alkynyl, N-methyl-N-methoxyamino, N-(2-methoxyethyl)-N-(2-cyanoethyl), a 5- or 6-membered nitrogenous heterocyclic ring which may contain several nitrogen atoms and optionally oxygen as ring members, $R^4$ denotes unsubstituted or halogen-substituted acyl of up to 4 carbon atoms, alkylsulfonyl or haloalkylsulfonyl of up to 4 carbon atoms in each alkyl or haloalkyl, the group —CO—NR$^5$R$^6$, R$^5$ and R$^6$ denoting hydrogen, linear or branched alkyl of up to 4 carbon atoms, or - but not simultaneously - phenyl, or R$^5$ and R$^6$ denoting, together with the nitrogen atom whose substituents they are, a 5- or 6-membered heterocyclic ring with further nitrogen atoms and an oxygen atom as ring members, or R$^4$ denotes the group —CO—Y—R$^7$, R$^7$ denoting linear or branched alkyl of up to 4 carbon atoms, phenyl or benzyl, and Y denoting oxygen or sulfur, and X denotes oxygen or sulfur, which are effective against pests, especially insects, mites and ticks; pesticides containing these phosphoric (phosphonic) acid esters as active ingredients; a process for producing these active ingredients; and a process for combating pests with these active ingredients.

9 Claims, No Drawings

PHOSPHORIC ACID ESTERS, COMPOSITION AND USE

The present invention relates to new phosphoric (phosphonic) acid esters, pesticides containing these compounds as active ingredients, and a process for manufacturing these compounds.

The phosphoric (phosphonic) acid esters according to the invention have the formula

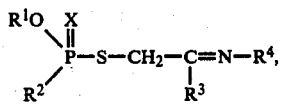

where $R^1$ denotes linear or branched alkyl of up to 4 carbon atoms, $R^2$ denotes linear or branched alkyl, alkoxy or alkylthio, each of up to 4 carbon atoms, mono- or dialkylamino of up to 4 carbon atoms in each alkyl, or phenyl, $R^3$ denotes linear or branched alkoxy or alkylthio of up to 4 carbon atoms, amino, mono- or dialkylamino of up to 4 carbon atoms in each alkyl, alkylalkoxyalkylamino of up to 4 carbon atoms in each alkyl or alkoxyalkyl, dialkoxyalkylamino of up to 4 carbon atoms in each alkoxyalkyl, alkylalkenylamino of up to 4 carbon atoms in each alkyl or alkenyl, alkylalkynylamino of up to 4 carbon atoms in each alkyl or alkynyl, N-methyl-N-methoxyamino, N-(2-methoxyethyl)-N-(2-cyanoethyl), a 5- or 6-membered nitrogenous heterocyclic ring which may contain several nitrogen atoms and optionally oxygen as ring members, $R^4$ denotes unsubstituted or halogen-substituted acyl of up to 4 carbon atoms, alkylsulfonyl or haloalkylsulfonyl of up to 4 carbon atoms in each alkyl or haloalkyl, the group —CO—$NR^5R^6$, $R^5$ and $R^6$ denoting hydrogen, linear or branched alkyl of up to 4 carbon atoms, or—but not simultaneously—phenyl, or $R^5$ and $R^6$ denoting, together with the nitrogen atom whose substituents they are, a 5- or 6-membered heterocyclic ring with further nitrogen atoms and an oxygen atom as ring members, or $R^4$ denotes the group —CO—Y—$R^7$, $R^7$ denoting linear or branched alkyl of up to 4 carbon atoms, phenyl or benzyl, and Y denoting oxygen or sulfur, and X denotes oxygen or sulfur.

Examples of linear or branched alkyl for $R^1$ and $R^2$ are methyl, ethyl, n-propyl, isopropyl, n-butyl, isobutyl, and sec-butyl, preferably methyl and ethyl; examples of alkoxy for $R^2$ and $R^3$ are methoxy, ethoxy, n-propoxy, isopropoxy, n-butoxy, and sec-butoxy, preferably methoxy, ethoxy, n-propoxy, and isopropxy; examples of alkylthio for $R^2$ and $R^3$ are methylthio, ethylthio, n-propylthio, isopropylthio, n-butylthio, isobutylthio, and sec-butylthio, preferably methylthio, ethylthio, n-propylthio, and isopropylthio; examples of alkyl and dialkylamino for $R^2$ and $R^3$ are methylamino, ethylamino, n-propylamino, isopropylamino, n-butylamino, isobutylamino, sec-butylamino, dimethylamino, diethylamino, di-n-propylamino, diisopropylamino, methylethylamino, methyl-n-propylamino, methylisopropylamino, and ethyl-n-propylamino, preferably methylamino, dimethylamino, ethylamino, diethylamino, isopropylamino, methylisopropylamino, di-n-propylamino, and diisopropylamino; examples of alkylalkoxyalkylamino or dialkoxyalkylamino for $R^3$ are methylmethoxyethylamino, ethylmethoxyethylamino, ethylmethoxyethylamino, ethylethoxyethylamino, bis-methoxyethylamino, and bis-ethoxyethylamino, preferably bis-methoxyethylamino, methylmethoxyethylamino, and ethylmethoxyethylamino; examples of alkylalkenylamino and alkylalkynylamino for $R^3$ are methylallylamino, ethylallylamino, methylpropargylamino, ethylpropargylamino, n-propylallylamino, isopropylallylamino, isopropylpropargylamino, and n-propylpropargylamino, preferably methylallylamino and methylpropargylamino; examples of suitable nitrogenous heterocyclic rings for $R^3$ are pyrrolidine, piperidine, morpholine, hexamethylenimine, imidazole, pyrazole, 1,2,4-triazole, and 1,3,4-triazole; examples of optionally halogen-substituted acyl for $R^4$ are chloro- or bromo-substituted acetyl or propionyl, e.g., chloroacetyl, dichloroacetyl, trichloroacetyl, bromoacetyl, and α-chloropropionyl, preferably acetyl and chloro-substituted acetyl; examples of alkylsulfonyl or haloalkylsulfonyl for $R^4$ are methylsulfonyl, ethylsulfonyl, n-propylsulfonyl, isopropylsulfonyl, n-butylsulfonyl, isobutylsulfonyl, sec-butylsulfonyl, and chloromethylsulfonyl, preferably methylsulfonyl and chloromethylsulfonyl; examples of carbamoyl for $R^4$ are N-methylcarbamoyl, N,N-dimethylcarbamoyl, N-ethylcarbamoyl, N,N-diethylcarbamoyl, N,N-phenylcarbamoyl, N-alkyl-N-phenylcarbamoyl or radicals of the formula —CO—$NR^5R^6$, where $R^5$ and $R^6$, together with the nitrogen atom whose substituents they are, form a pyrrolidine, morpholine, piperidine, imidazole, pyrazole or triazole ring; examples of alkoxycarbonyl and alkylmercaptocarbonyl for $R^4$ are methoxycarbonyl, ethoxycarbonyl, n-propoxycarbonyl, isopropoxycarbonyl), sec-butoxycarbonyl, methylmercaptocarbonyl, ethylmercaptocarbonyl, n-propylmercaptocarbonyl, isopropylmercaptocarbonyl, and sec-butylmercaptocarbonyl.

Preferred phosphoric (phosphonic) acid esters of the formula I are those in which $R^1$ is ethyl, $R^2$ is ethoxy or n-propylthio, $R^3$ is mono- or dialkylamino of up to 4 carbon atoms in each alkyl, alkylalkenylamino of up to 4 carbon atoms in each alkyl or alkenyl, alkylalkynylamino of up to 4 carbon atoms in each alkyl or alkynyl, or morpholinyl, $R^4$ is methylsulfonyl, chloromethylsulfonyl, or methoxycarbonyl, and X is oxygen or sulfur.

The new phosphoric (phosphonic) acid esters of the formula I are obtained by reaction of compounds of the formula

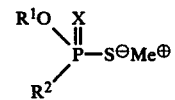

with compounds of the formula

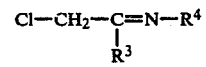

at from 0° to 150° C. and in the presence of a solvent. In the above formulae the radicals $R^1$, $R^2$, $R^3$, $R^4$ and X have the above meanings. Me denotes an equivalent of an inorganic or organic cation, e.g., an alkali metal ion, such as sodium or potassium, one equivalent of an alkaline earth metal ion, such as calcium or magnesium, or an unsubstituted or substituted ammonium ion, such as alkylammonium, dialkylammonium or trialkylammonium.

The reaction is carried out in diluents inert to the reactants. Examples of suitable diluents are water; ethers, such as tetrahydrofuran, dioxane, diisopropyl ether, diethyl ether, and diglycol dimethyl ether; ketones, such as acetone, methyl ethyl ketone, and diethyl ketone; aromatic hydrocarbons, such as toluene, nitrobenzene, xylenes, and chlorobenzenes; nitriles, such as acetonitrile; chlorinated aliphatic hydrocarbons, such as methylene chloride, ethylene chloride, and chloroform; dimethylformamide and dimethyl sulfoxide. Mixtures of these diluents may also be used.

The reaction temperature may be varied within a wide range. Generally, the temperature is from 0° to 150° C., preferably from 25° to 60° C.

To carry out the process, the starting materials are usually used in equimolar amounts; however, an excess of the one or the other component is not disadvantageous. The end products are obtained in the form of oils which crystallize upon standing for a fairly long time. Their refractive index or melting point is given by way of characterization.

Examples of phosphorylation components of the formula II are ammonium-O,O-dimethylthiophosphate, ammonium-O,O-dimethyldithiophosphate, ammonium-O,O-diethylthiophosphate, ammonium-O,O-diethyldithiophosphate, ammonium-O,O-diisopropylthiophosphate, ammonium-O,O-diisopropylthiophosphate, and the corresponding sodium potassium, calcium and dimethylammonium salts.

The compounds of the formula III used as starting materials may be obtained in known manner by reaction of chloroacetonitrile with alcohols, mercaptans or amines of the formula R³H, where R³ has the above meanings, and hydrogen chloride, and by reaction of the chloroacetimino ester hydrochloride thus obtained with an acyl chloride, carbamoyl chloride or a sulfo chloride of the formula R⁴Cl, where R⁴ has the above meanings, in accordance with the following equations:

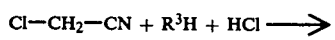  (a)

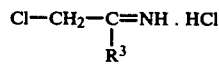

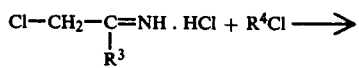  (b)

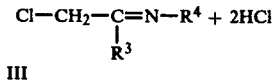

III

The reaction according to equation (a) takes place at room temperature in the presence of an inert organic diluent. Suitable diluents are those recommended for the reaction of compounds of the formula III with the salts of (di)thiophosphates of the formula II, with the exception of the ketones and the nitriles.

The reaction according to equation (b) is carried out in the indifferent organic diluents suitable for the reaction according to equation (a), in the presence of an organic base, e.g., a trialkylamine, such as triethylamine, an N,N-dialkylaniline, such as N,N-dimethylaniline or N,N-diethylaniline, or a heterocyclic amine, such as pyridine or quinoline. The reaction may also be carried out in a two-phase system consisting of water and a water-immiscible solvent, in the presence of one of the abovementioned organic bases or of an inorganic base, e.g., an alkali metal hydroxide, such as sodium hydroxide or potassium hydroxide, an alkali metal carbonate, such as sodium carbonate or potassium carbonate, or an alkali metal bicarbonate, such as sodium bicarbonate or potassium bicarbonate.

The reaction temperature may be from −40° to +100° C.; the preferred temperature range is from −20° to +50° C.

The reactants in the reactions according to equations (a) and (b) may be employed in equimolar amounts; however it is advantageous to use a slight excess of the cheaper reaction component.

The products obtained in accordance with (a) and (b) need not be isolated; they can be reacted in a one-vessel process to give the end products of the formula I.

The following examples illustrate the preparation of the starting materials of the formula III.

EXAMPLE 1

150 g of chloroacetonitrile and 65 g of absolute methanol are diluted with 300 ml of absolute diethyl ether, and the resulting mixture is then gassed at room temperature with dry hydrogen chloride; after the solvent has been distilled off, there is obtained 282 g of the compound

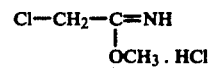

having a melting point of 78°-80° C.

EXAMPLE 2

152 g of isopropyl mercaptan and 150 g of chloroacetonitrile are dissolved in 1,000 ml of dry methylene chloride; at 20° to 30° C. the mixture is gassed with dry hydrogen chloride until it is saturated. After the volatiles have been distilled off, 350 g of the compound

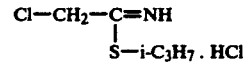

is obtained, which melts, with decomposition, at 105° C.

EXAMPLE 3

At 0° C., 2.2 g of sodium methylate is added to a solution of 75.5 g of chloroacetonitrile in 200 ml of absolute methanol. The temperature of the mixture is allowed to rise to 25° C. and it is then stirred for 30 minutes. There is then added 2.4 g of glacial acetic acid and subsequently 81.5 g of dimethylamine hydrochloride is introduced in portions. The temperature of the mixture is allowed to rise to 50° C., at which temperature it is stirred for a further 4 hours. After concentration, there is obtained 145 g of the compound

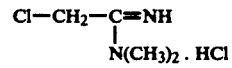

having a melting point of 179° to 181° C.

EXAMPLE 4

At from −10° to 0° C., 31.4 g of N,N-dimethylchloroacetamidine hydrochloride is added to 16 g of sodium hydroxide, dissolved in 150 ml of water, and 300 ml of methylene chloride; over a period of 30 minutes, 25.4 g of methanesulfonyl chloride is then dripped in. The mixture is subsequently stirred for 30 minutes at 0° C., the phases are then separated, and the organic phase is washed twice, each time with 100 ml of water, dried over sodium sulfate, and concentrated in vacuo. There is obtained 27.8 parts of the compound

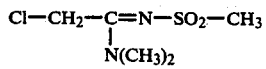

having a melting point of 65° to 67° C.

EXAMPLE 5

Analogously to Example 4, there is obtained from 31.4 g of N,N-dimethylchloroacetamidine hydrochloride and 17.3 g of acetyl chloride 19 g of the compound

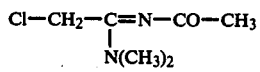

as a yellowish oil; $n_D^{25}$: 1.5190.

EXAMPLE 6

Analogously to Example 4, there is obtained from 31.4 g of N,N-dimethylchloroacetamidine hydrochloride and 31.4 g of chloromethanesulfonyl chloride 40 g of the compound

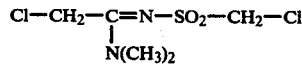

having a melting point of 70° to 72° C.

EXAMPLE 7

At from −5° to 0° C., 80.8 g of triethylamine is added to a suspension of 75.2 g of S-isopropylchloroacetimine thioether hydrochloride in 400 ml of methylene chloride; subsequently, 74.7 g of trichloroacetyl chloride is dripped in. The mixture is then stirred for 30 minutes at room temperature. It is then washed 3 times with water, dried over sodium sulfate, and concentrated; there is obtained 107 g of the compound

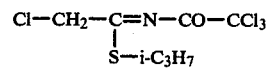

as an oily liquid; $n_D^{25}$: 1.5435.

EXAMPLE 8

Analogously to Example 7, there is obtained from 51.6 g of O-isopropylchloroacetimine ether and 35.4 g of methanesulfonyl chloride 40 g of the compound

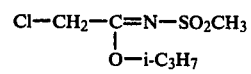

$n_D^{25}$: 1.4670.

The preparation of the novel phosphoric (phosphonic) acid esters of the formula I is illustrated in the following example.

EXAMPLE 9

At from 30° to 40° C., a solution of 9.9 g of N,N-dimethyl-N'-methylsulfonylchloroacetamidine in 50 ml of acetone is dripped into a solution of 11.2 g of ammonium-O,O-diethylthiophosphate in 75 ml of acetone. The mixture is then stirred at from 60° to 70° C. for 3 to 4 hours. It is then filtered and the filtrate is concentrated; the residue is taken up in methylene chloride and washed 3 times, each time with 20 ml of water. The organic phase is dried over sodium sulfate and the solvent distilled off.

There is obtained 15 g of the compound

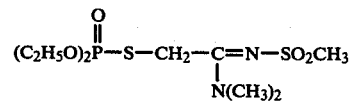

as a pale yellow oil which solidifies on standing for a fairly long period of time to almost colorless crystals of melting point 55° to 57° C.

The following compounds of the formula

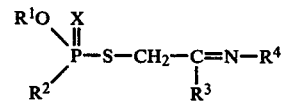

were prepared by the process explained in Example 9:

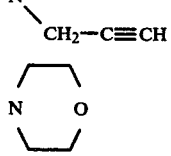

| No. | R$^1$ | R$^2$ | R$^3$ | R$^4$ | X | $n_D^{25}$ (m.p.°C.) |
|---|---|---|---|---|---|---|
| 1 | C$_2$H$_5$ | C$_2$H$_5$O | N(CH$_3$)$_2$ | SO$_2$CH$_3$ | O | (55–57) |
| 2 | C$_2$H$_5$ | C$_2$H$_5$O | N(CH$_3$)$_2$ | COCH$_3$ | S | 1.5512 |
| 3 | C$_2$H$_5$ | C$_2$H$_5$O | N(CH$_3$)$_2$ | COCH$_3$ | O | 1.4733 |
| 4 | C$_2$H$_5$ | C$_2$H$_5$O | N(CH$_3$)$_2$ | COCHCl$_2$ | S | 1.5578 |
| 5 | C$_2$H$_5$ | C$_2$H$_5$O | N(CH$_3$)$_2$ | COCHCl$_2$ | O | 1.5168 |
| 6 | C$_2$H$_5$ | C$_2$H$_5$O | N(CH$_3$)$_2$ | COCCl$_3$ | S | 1.5565 |
| 7 | C$_2$H$_5$ | C$_2$H$_5$O | N(CH$_3$)$_3$ | COCCl$_3$ | O | 1.5322 |
| 8 | C$_2$H$_5$ | C$_2$H$_5$O | N(CH$_3$)(CH$_2$–C≡CH) | SO$_2$CH$_2$Cl | S | 1.5430 |
| 9 | C$_2$H$_5$ | C$_2$H$_5$O | morpholino | SO$_2$CH$_2$Cl | S | 1.5502 |

-continued

| No. | R¹ | R² | R³ | R⁴ | X | $n_D^{25}$ (m.p.°C.) |
|---|---|---|---|---|---|---|
| 10 | C₂H₅ | C₂H₅O | (morpholino, N-O ring) | SO₂CH₂Cl | O | 1.5205 |
| 11 | C₂H₅ | C₂H₅O | N(CH₃)₂ | SO₂CH₃ | S | 1.5310 |
| 12 | C₂H₅ | C₂H₅O | N(CH₃)₂ | SO₂CH₂Cl | O | (52–53) |
| 13 | C₂H₅ | C₂H₅O | N(CH₃)₂ | SO₂CH₂Cl | S | (68) |
| 14 | CH₃ | N(CH₃)₂ | N(CH₃)₂ | SO₂CH₂Cl | O | 1.5415 |
| 15 | CH₃ | N(CH₃)₂ | N(CH₃)₂ | COCHCl₂ | O | 1.5430 |
| 16 | CH₃ | N(CH₃)₂ | N(CH₃)₂ | COCCl₃ | O | 1.5520 |
| 17 | C₂H₅ | C₂H₅O | OCH₃ | SO₂CH₃ | S | 1.5400 |
| 18 | C₂H₅ | C₂H₅O | i-C₃H₇ | COCCl₃ | O | 1.4750 |
| 19 | CH₃ | N(CH₃)₂ | i-C₃H₇O | COCCl₃ | O | 1.4875 |
| 20 | CH₃ | CH₃O | N(CH₃)₂ | SO₂CH₂Cl | O | (58–60) |
| 21 | CH₃ | CH₃ | N(CH₃)₂ | SO₂CH₃ | S | 1.5690 |
| 22 | C₂H₅ | C₆H₅ | N(CH₃)₂ | SO₂CH₂Cl | S | 1.5992 |
| 23 | CH₃ | CH₃ | N(CH₃)₂ | COCH₃ | S | 1.5670 |
| 24 | CH₃ | CH₃O | N(CH₃)₂ | COCHCl₂ | S | 1.5600 |
| 25 | C₂H₅ | C₆H₅ | N(CH₃)₂ | COCHCl₂ | S | 1.6025 |
| 26 | CH₃ | CH₃ | N(CH₃)₂ | COCCl₃ | S | 1.5193 |
| 27 | C₂H₅ | C₆H₅ | N(CH₃)₂ | COCCl₃ | S | 1.5950 |
| 28 | CH₃ | N(CH₃)₂ | NH₂ | SO₂CH₂Cl | O | (66–69) |
| 29 | C₂H₅ | C₂H₅—CH(CH₃)—S | N(CH₃)₂ | SO₂CH₃ | O | 1.5448 |
| 30 | C₂H₅ | (CH₃)₂CH—CH₂—S | N(CH₃)₂ | SO₂CH₃ | O | 1.5418 |
| 31 | C₂H₅ | C₂H₅—CH(CH₃)—S | N(CH₃)₂ | SO₂CH₂Cl | O | 1.5504 |
| 32 | C₂H₅ | n-C₃H₇S | N(CH₃)₂ | SO₂CH₃ | O | 1.5475 |
| 33 | C₂H₅ | n-C₃H₇S | N(CH₃)₂ | SO₂CH₂Cl | O | 1.5508 |
| 34 | C₂H₅ | n-C₃H₇S | N(CH₃)₂ | COCCl₃ | O | 1.5530 |
| 35 | C₂H₅ | n-C₃H₇S | N(CH₃)₂ | COCH₃ | O | 1.5290 |
| 36 | C₂H₅ | n-C₃H₇S | i-C₃H₇O | COCH₃ | O | 1.4900 |
| 37 | C₂H₅ | n-C₃H₇O | i-C₃H₇O | COCCl₃ | O | 1.5070 |
| 38 | C₂H₅ | C₂H₅O | C₂H₅O | COCHCl₂ | S | 1.5180 |
| 39 | C₂H₅ | C₂H₅O | i-C₃H₇O | COCH₃ | S | 1.4820 |
| 40 | C₂H₅ | C₂H₅O | i-C₃H₇O | COCCl₃ | S | 1.5240 |
| 41 | C₂H₅ | C₂H₅O | i-C₃H₇S | COCCl₃ | S | 1.5450 |
| 42 | C₂H₅ | C₂H₅O | i-C₃H₇S | COCCl₃ | O | 1.5030 |
| 43 | C₂H₅ | C₂H₅O | CH₃S | COCHCl₂ | O | 1.5270 |
| 44 | C₂H₅ | C₂H₅O | CH₃S | COCHCl₂ | S | 1.5450 |
| 45 | C₂H₅ | C₂H₅O | NH₂ | SO₂CH₂Cl | S | 1.5560 |
| 46 | C₂H₅ | C₂H₅O | NH₂ | SO₂CH₂Cl | O | 1.5210 |
| 47 | C₂H₅ | C₂H₅O | NH(CH₃) | SO₂CH₂Cl | S | (76–77) |
| 48 | C₂H₅ | C₂H₅O | NH(CH₃) | SO₂CH₂Cl | O | 1.5205 |
| 49 | C₂H₅ | C₂H₅O | N(C₂H₅)₂ | SO₂CH₂Cl | O | 1.5080 |
| 50 | C₂H₅ | C₂H₅O | N(C₂H₅)₂ | SO₂CH₂Cl | S | 1.5265 |
| 51 | C₂H₅ | C₂H₅O | CH₃—N—i-C₃H₇ | SO₂CH₂Cl | O | 1.5018 |
| 52 | C₂H₅ | C₂H₅O | CH₃—N—i-C₃H₇ | SO₂CH₂Cl | S | 1.5265 |
| 53 | C₂H₅ | C₂H₅O | NH—i-C₃H₇ | SO₂CH₂Cl | O | 1.5308 |
| 54 | C₂H₅ | C₂H₅O | NH—i-C₃H₇ | SO₂CH₂Cl | S | 1.4950 |
| 55 | C₂H₅ | C₂H₅O | N(CH₂CH₂OCH₃)(CH₂—CH₂CN) | SO₂CH₂Cl | S | 1.5270 |
| 56 | C₂H₅ | C₂H₅ | N(CH₂CH₂OCH₃)(CH₂—CH₂CN) | SO₂CH₂Cl | O | 1.4980 |
| 57 | C₂H₅ | C₂H₅O | N(CH₃)₂ | CONHCH₃ | O | 1.5040 |
| 58 | C₂H₅ | C₂H₅O | N(CH₃)₂ | COOCH₃ | O | 1.5100 |
| 59 | C₂H₅ | C₂H₅O | N(CH₃)₂ | CONHCH₃ | S | 1.5488 |
| 60 | C₂H₅ | C₂H₅O | N(CH₃)₂ | COOCH₃ | S | 1.5425 |
| 61 | CH₃ | CH₃ | N(CH₃)₂ | COOCH₃ | S | 1.5695 |
| 62 | C₂H₅ | C₂H₅O | N(CH₃)₂ | COSC₂H₅ | S | 1.5675 |
| 63 | C₂H₅ | C₂H₅O | N(CH₃)₂ | COSC₂H₅ | O | 1.5380 |
| 64 | CH₃ | CH₃ | N(CH₃)₂ | COSC₂H₅ | S | 1.5975 |

The novel phosphoric (phosphonic) acid esters of the formula I are eminently suitable for combating pests, especially mites and ticks.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Otiorrhynchus ovatus, Hylobies abietis, Byctiscus betulae, Anthonomus pomorum, Anthonomus grandis, Ceuthorrhynchus assimilis, Ceuthorrhynchus*

*napi, Sitophilus granaria, Anisandrus dispar, Ips typographus,* and *Blastophagus piniperda;* examples from the Diptera order are *Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae,* and *Pegomya hyoscyami;* examples from the Hymenoptera order are *Athalia rosae, Haplocampa minuta, Monomorium pharaonis, Solenopsis geminata, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna vari estris, Phyllopertha horticola, Popillia japonica, Melolontha melolontha, Melolontha hippocastani, Amphimallus solstitialis, Crioceris asparagi, Lema Melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus,* and *Atta sexdens;* examples from the Hepteroptera order are *Nezara viridula, Eurygaster integriceps, Blissus leucopterus, Dysdercus cingulatus, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Eriosoma lanigerum, Pemphigus bursarius, Dreyfusia nordmannianae, Dreyfusia piceae, Adelges laricis,* and *Viteus vitifolii;* an example from the Isoptera order is *Reticulitermes lucifugus.*

Examples of mites and ticks (Acarina) belonging to the Arachnida class are *Tetranychus urticae, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

The compounds according to the invention may be successfully employed as pesticides for crop protection, and in the hygiene, stores protection and veterinary sectors.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensation products of sulfonated naphthalene and naphthalene and derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol and ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol and ether acetal, sorbitol esters, lignin, sulfate waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formullations containing up to 95% of active ingredient, or even the 100% active ingredient.

Examples of formulations are given below.

I.

250 g of active ingredient no. 1
30 g of calcium dodecylbenzenesulfonate
70 g of ethoxylated castor oil 150 g of N-methylpyrrolidone
xylene makeup to 1,000 ml.

II.
250 g of active ingredient no. 14
10 g of calcium dodecylbenzensulfonate
90 g of ethoxylated castor oil
cyclohexanone makeup to 1,000 ml III.
3 parts by weight of active ingredient no. 32 is intimately mixed with 97 parts by weight of particulate kaolin. A dust is obtained containing 3% by weight of the active ingredient.

IV.
30 parts by weight of active ingredient no. 58 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

There may be added to the individual active ingredients or mixtures thereof (if desired, immediately before use (tankmix)) oils of various types, herbicides, fungicides, insecticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropane, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)oxy]-1-thiooxamidate, N-(2-methyl-4-chlorophenyl)-N'N'-dimethylformamidine, tetrachlorothiophene, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramide, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-dimethyl-S-(2-ethylsulfynylethyl)-phosphorothioate, O,O-diethylthiophosphoryliminophenyl)-acetonitrile, O,O-diethyl-S-(2-chloro-1-phthalimidoethyl)-phosphorodithioate, O,O-diethyl-S-[6-chlorobenzoxazolon-(2)-yl-(3)-9-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, γ-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide.

The following examples demonstrate the biological action. The agent used for comparison purposes is O,O-dimethyl-S-(1,2-dicarbethoxyethyl)-dithiophosphoric acid ester (German 847,897). The active ingredients are numbered as in the foregoing table.

EXAMPLE A

Contact action on aphids (*Aphis fabae*); spray experiment

Potton bean plants (*Vivia faba*) heavily infected with aphid colonies are sprayed to runoff in a spray chamber with aqueous formulations containing various active ingredient concentrations.

The kill rate is determined after 24 hours.

| Active ingredient | Kill rate at active ingredient concentrations (wt %) of | | | |
|---|---|---|---|---|
| | 0.01 | 0.005 | 0.0025 | 0.001 |
| 1 | 100 | 90 | <60 | |
| 3 | 100 | 100 | 70 | |
| 5 | 100 | 90 | <60 | |
| 7 | 100 | 95 | <60 | |
| 10 | 100 | 100 | 100 | 70 |
| 12 | 100 | 100 | 100 | 100 |
| 13 | 100 | 90 | <60 | |

-continued

| Active ingredient | Kill rate at active ingredient concentrations (wt %) of | | | |
|---|---|---|---|---|
| | 0.01 | 0.005 | 0.0025 | 0.001 |
| 36 | 100 | 100 | <60 | |
| 43 | 100 | 100 | 60 | |
| 48 | 100 | 95 | <60 | |
| 49 | 100 | 95 | <60 | |
| 58 | 100 | 95 | <60 | |
| Comparative agent | 100 | 60 | | |

EXAMPLE B

Systemic action on aphids (*Aphis fabae*); watering experiment

The soil around heavily aphid-infected bean plants in plastic pots (8 cm in diameter) filled with 300 g of compost is watered with 20 ml of aqueous formulations containing various active ingredient concentrations.
The kill rate is determined after 48 hours.

| Active ingredient | Kill rate at active ingredient concentrations (wt %) of | | |
|---|---|---|---|
| | 0.02 | 0.01 | 0.005 |
| 1 | 100 | 100 | 90 |
| 3 | 100 | 100 | 60 |
| 5 | 100 | 60 | |
| 7 | 100 | 90 | |
| 10 | 100 | 100 | 50 |
| 11 | 100 | 90 | >50 |
| 12 | 100 | 100 | 90 |
| 45 | 100 | 50 | |
| 49 | 100 | 90 | |
| 57 | 100 | 60 | |
| 58 | 100 | 100 | 90 |
| Comparative agent | ineffective | | |

EXAMPLE C

Action on red spider mite (*Tetranychus telarius*); highly resistant strain

Potton bush beans which have developed the first pair of true leaves and are heavily infested with all stages of the red spider mite (*Tetranychus telarius*) are sprayed to runoff with aqueous active ingredient formulations in a spray chamber.
The action is determined after 5 days.

| Active ingredient | Kill rate (%) at active ingredient concentrations (wt %) of | | |
|---|---|---|---|
| | 0.02 | 0.01 | 0.005 |
| 1 | 100 | | |
| 9 | 100 | | |
| 12 | 100 | 90 | |
| 13 | 100 | 100 | 95 |
| 32 | 100 | 95 | |
| 33 | 100 | 90 | |
| Comparative agent | ineffective | | |

EXAMPLE D

Contact action and effect of ingested food on caterpillars of the diamondback moth (*Plutella maculipennis*)

Leaves of young cabbage plants are dipped for 3 seconds in aqueous emulsions of the active ingredients and, after briefly having allowed excess liquid to drip off, are placed on a moist filter paper in a Petri dish. Subsequently, 10 caterpillars of the diamondback moth in the 4th stage are placed on each leaf.
The kill rate is determined after 48 hours.

| Active ingredient | Kill rate (%) at active ingredient concentrations (wt %) of | | |
|---|---|---|---|
| | 0.02 | 0.01 | 0.005 |
| 8 | 100 | 100 | 100 |
| 13 | 100 | 90 | |
| 32 | 100 | 100 | 85 |
| 33 | 100 | 100 | 80 |
| 48 | 100 | 80 | |
| 56 | 100 | 80 | |

EXAMPLE E

Contact action on ticks (*Ornithodorus moubata*)

Ticks in the 3rd larval stage are placed in paper bags which are then dipped for 3 seconds in the emulsion under investigation. The bags are then suspended. The action is assessed after 48 hours.

| Active ingredient | Kill rate (%) at active ingredient concentrations (wt %) of | | | |
|---|---|---|---|---|
| | 0.02 | 0.01 | 0.005 | 0.0025 |
| 11 | 100 | 80 | | |
| 1 | 100 | 100 | 100 | |
| 13 | 100 | 100 | 100 | |
| 12 | 100 | 40 | | |
| 3 | 100 | 80 | | |
| 6 | 100 | 100 | | |
| 7 | 100 | 80 | | |
| 57 | 100 | 80 | | |
| 46 | 100 | 80 | | |
| 47 | 100 | 100 | 80 | |
| 48 | 100 | 100 | 100 | 100 |
| 50 | 100 | 100 | 100 | 80 |
| 49 | 100 | 100 | 80 | |
| 54 | 100 | 80 | | |
| 52 | 100 | 100 | | |
| 51 | 100 | 100 | | |
| 55 | 100 | 100 | | |
| 56 | 100 | 100 | | |
| 8 | 100 | 100 | | |
| 9 | 100 | 100 | | |
| 10 | 100 | 100 | 100 | |
| 14 | 100 | 80 | | |
| 36 | 100 | 80 | | |
| 43 | 100 | 100 | | |
| Comparative agent | ineffective | | | |

We claim:
1. A phosphoric (phosphonic) acid ester of the formula

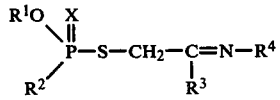

I, where $R^1$ denotes linear or branched alkyl of up to 4 carbon atoms, $R^2$ denotes linear or branched alkoxy or alkylthio, each of up to 4 carbon atoms $R^3$ denotes amino, mono- or di-alkylamino of up to 4 carbon atoms in each alkyl, alkylalkoxyalkyl-amino of up to 4 carbon atoms in each alkyl or alkoxyalkyl, di-alkoxyalkylamino of up to 4 carbon atoms in each alkoxyalkyl, alkylalkenylamino of up to 4 carbon atoms in each alkyl or alkenyl, alkylalkynylamino of up to 4 carbon atoms in each alkyl or alkynyl, N-methyl-N-methoxyamino, $R^4$ denotes alkylsulfonyl or haloalkylsulfonyl of up to 4 carbon atoms in each alkyl or haloalkyl, and X denotes oxygen or sulfur.

2. A phosphoric (phosphonic) acid ester of the formula I, wherein $R^1$ denotes ethyl, $R^2$ denotes ethoxy or n-propylthio, $R^3$ denotes mono- or dialkylamino of up to 4 carbon atoms in each alkyl, alkylalkenylamino of up to 4 carbon atoms in each alkyl or alkenyl or alkylalkynylamino of up to 4 carbon atoms in each alkyl or alkynyl, $R^4$ denotes methylsulfonyl or chloromethylsulfonyl, and X denotes oxygen or sulfur.

3. The compound of the formula

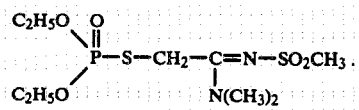

4. The compound of the formula

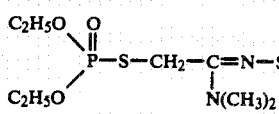

5. The compound of the formula

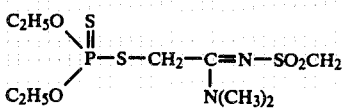

6. A phosphoric (phosphonic) acid ester as set forth in claim 1 wherein X is oxygen.

7. A phosphoric (phosphonic) acid ester as set forth in claim 2 wherein X is oxygen.

8. Pesticides for insects, mites and ticks comprising a solid and/or liquid carrier and an amount of a phosphoric (phosphonic) acid ester of the formula I sufficient to kill said insects, mites or ticks.

9. A process for combating insects, mites and ticks wherein a lethal amount of a phosphoric (phosphonic) acid ester of the formula I is allowed to act on the insects, mites or ticks or their habitat.

* * * * *